United States Patent
Hart et al.

(10) Patent No.: US 9,782,145 B2
(45) Date of Patent: *Oct. 10, 2017

(54) ELECTRONIC CATHETER STETHOSCOPE

(71) Applicants: University of South Florida, Tampa, FL (US); The Charles Stark Draper Laboratory, Inc., Cambridge, MA (US)

(72) Inventors: Stuart Hart, Tampa, FL (US); Gerard Michael DiLeo, Palmetto, FL (US); Alfredo Weitzenfeld, Tampa, FL (US); Philip James Hipol, Tampa, FL (US); Mark Xavier Sweeney, Valrico, FL (US); Francy Lorena Sinatra, Temple Terrace, FL (US); Kevin Andrew Hufford, St. Petersburg, FL (US); Susana K. Lai-Yuen, Tampa, FL (US)

(73) Assignees: University of South Florida, Tampa, FL (US); The Charles Stark Draper Laboratory, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,001

(22) Filed: Nov. 28, 2016

(65) Prior Publication Data

US 2017/0071566 A1 Mar. 16, 2017

Related U.S. Application Data

(63) Continuation of application No. 13/621,566, filed on Sep. 17, 2012, now Pat. No. 9,504,440, which is a
(Continued)

(51) Int. Cl.
*A61B 7/04* (2006.01)
*A61B 7/02* (2006.01)
(Continued)

(52) U.S. Cl.
CPC ............... *A61B 7/04* (2013.01); *A61B 5/033* (2013.01); *A61B 7/023* (2013.01); *A61B 5/4362* (2013.01); *A61B 2503/02* (2013.01)

(58) Field of Classification Search
CPC ....................................... A61B 7/04
See application file for complete search history.

(56) References Cited

U.S. PATENT DOCUMENTS

| | | |
|---|---|---|
| 4,383,534 A | 5/1983 | Peters |
| 5,000,185 A | 3/1991 | Yock |

(Continued)

FOREIGN PATENT DOCUMENTS

WO 2004045404 A1 6/2004

OTHER PUBLICATIONS

International Search Report and Written Opinion issued Dec. 7, 2011 for corresponding International Patent Application No. PCT/US2011/028519 with an International filing date of Mar. 15, 2011.
(Continued)

*Primary Examiner* — Rochelle Turchen
(74) *Attorney, Agent, or Firm* — Nilay J. Choksi; Smith & Hopen, P.A.

(57) ABSTRACT

An electronic catheter stethoscope measures and analyzes acoustic fields and dynamic pressure variations in the gaseous or liquid fluid inside a conventional medical catheter that is positioned in a patient's urologic, digestive, reproductive, cardiovascular, neurological or pulmonary system. Measurement transducers are installed in a housing connectable to multiple preselected medical catheters. The transducers detect bodily functions that are transmitted to the preselected catheter from within the body. The transducers, housing, electrical interface and signal processing electronics are positioned outside the body.

20 Claims, 4 Drawing Sheets

Related U.S. Application Data continuation of application No. PCT/US2011/028519, filed on Mar. 15, 2011.

(60) Provisional application No. 61/313,921, filed on Mar. 15, 2010.

(51) Int. Cl.
*A61B 5/03* (2006.01)
*A61B 5/00* (2006.01)

(56) References Cited

U.S. PATENT DOCUMENTS

| | | |
|---|---|---|
| 5,263,485 A | 11/1993 | Hickey |
| 6,434,418 B1 | 8/2002 | Neal et al. |
| 7,949,389 B2 | 5/2011 | Wolfberg et al. |
| 2003/0195428 A1 | 10/2003 | Brockway et al. |
| 2007/0015994 A1 | 1/2007 | Hong et al. |
| 2008/0171942 A1 | 7/2008 | Brockway et al. |
| 2009/0192396 A1 | 7/2009 | Hayes-Gill et al. |
| 2010/0030095 A1 | 2/2010 | Yu |
| 2010/0280363 A1 | 11/2010 | Skarda et al. |

OTHER PUBLICATIONS

International Preliminary Report on Patentability issued Sep. 27, 2012 for corresponding International Patent Application No. PCT/US2011/028519 with an International filing date of Mar. 15, 2011.
Official Action from Canadian Intellectual Property Office with notification date of Oct. 26, 2015 for corresponding Canadian Application No. 2,803,065 by same inventors.
Extended European Search Report issued on Jun. 6, 2017 in corresponding European Application No. 11756854.3, for Applicant University of South Florida.

ELECTRONIC CATHETER STETHOSCOPE

CROSS-REFERENCE TO RELATED APPLICATIONS

This application is a continuation of and claims priority to U.S. Nonprovisional patent application Ser. No. 13/621,566, entitled "Electronic Catheter Stethoscope", filed Sep. 17, 2012, now U.S. Pat. No. 9,504,440, which is a continuation of and claims priority to International Patent Application No. PCT/US2011/028519, entitled "Electronic Catheter Stethoscope", filed Mar. 15, 2011, which claims priority to U.S. Provisional Patent Application No. 61/313,921, entitled "Electronic Catheter Stethoscope", filed Mar. 15, 2010, all of which are incorporated herein by reference in their entireties.

BACKGROUND OF THE INVENTION

1. Field of the Invention

This invention relates to medical devices. More particularly, it relates to a device that monitors, measures and analyzes a variety of bodily functions.

2. Description of the Prior Art

Fetal heart tones and labor contractions are measured using sensors or instruments that are placed externally on the mother's body. This method is illustrated in prior art FIG. 1.

U.S. Patent Application Publication Nos. 2009/0259133A1 and 2009/0192396A1 disclose the positioning of electrocardiogram (ECG) electrodes on the mother's abdomen to detect the fetal heart tone. Systems of this type rely on the detection of electrical impulses that originate from the heart muscles of the mother, the fetus, or both, myoelectric sensors capable of detecting muscle contractions, or Doppler ultrasound to detect heart movement.

There are a number of disadvantages to placing external monitors on the mother's body to monitor the fetal heart rate and intrauterine contractions as follows:

The fetal heart rate sensor performance can be compromised by:
  Poor placement of sensors on mother's abdomen
  Excessive amniotic fluid
  Obese mother
  Small or multiple babies
  Movement of the baby out from under the sensor or sensors
  Detection of mother's pulse instead of baby's pulse
  The sensors are prone to falling off or moving, so the mother must remain still The contraction sensor performance is compromised because it:
  Can only detect frequency and duration of contractions
  Cannot provide direct measurement of intrauterine pressure intensity
  Cannot provide comparative measurements of a series of contractions Fetal heart tones and labor contractions are also measured using sensors or instruments that are positioned in the mother's uterus and on the baby's head. This method is illustrated in FIG. 2.

There are a number of disadvantages to using an internal monitor installed within the mother's uterus or on the baby as follows:
  The cervix must be dilated prior to placement of the monitors
  Membranes must be ruptured to place monitor which commits mother/baby to delivery
  Increased risk of infection to the baby
  Increased risk of bruising of the baby's scalp
  Possible uterine perforation/rupture
  Potential for placental separation U.S. Pat. No. 6,434,418 discloses an instrumented catheter inserted into the bladder or rectum including a catheter balloon instrumented with pressure or myoelectric sensors to measure intrauterine pressure or detect contractions and a catheter tip instrumented with microphone, electrode or Doppler ultrasound probe to measure fetal heart rate. This method requires placement of electronic instrumentation within the body, it requires high-cost manufacturing of catheters having electronic instruments within them, it requires additional and non-standard procedures and personnel for placement of the catheter, and it requires that the entire catheter system be sterilized for re-use.

There are no known commercial products or technologies that non-invasively detect physiologic bladder changes during surgical procedures or provide direct measurement of acoustic fields and pressure variations within the bladder that could suggest bladder or ureteral injury.

Conventional blood pressure monitoring devices provide only pressure time histories of blood flow and do not measure to a sufficiently high frequency range acoustic or pressure variations that can be used to detect cardiovascular anomalies. Patent applications such as U.S. Patent Application Publication No. 2010/00030095 disclose acoustic monitors and electronic stethoscopes to detect cardiovascular anomalies. However, the known devices do not provide direct measurement of acoustic fields and dynamic pressure variations of the blood within the blood vessels.

The known commercial products or technologies that enable direct measurement of acoustic fields and dynamic pressure variations due to respiration and blood flow within the lungs require the installation of measurement transducers within the lungs.

The prior art devices that enable direct measurement of acoustic fields and dynamic pressure variations due to digestion and blood flow within the stomach or upper digestive tract require the installation of measurement transducers within the stomach or upper digestive tract.

Commercial products or technologies that enable direct measurement of acoustic fields and dynamic pressure variations due to digestion and blood flow within the colon require the installation of measurement transducers within the colon.

What is needed, then, is a medical device that enables direct measurement of acoustic fields and dynamic pressure variations within such body parts without requiring that transducers by positioned within said body parts.

However, in view of the art considered as a whole at the time the present invention was made, it was not obvious to those of ordinary skill in the art that a medical device that enables direct measurement of acoustic fields and dynamic pressure variations within body parts without requiring transducers positioned within said body parts was needed nor was it obvious how such a device could be provided.

SUMMARY OF THE INVENTION

The present invention includes an electronic catheter stethoscope that enables the measurement and analysis of acoustic fields and dynamic pressure variations in the gaseous or liquid fluids inside a standard medical catheter that may be installed in a patient's urologic, digestive, reproductive, cardiovascular, neurological or pulmonary system to monitor a patient's heart beat, fetal heart beat, breathing, labor contractions, ureteral flow and physiology of the bladder, digestive, urologic, pulmonary, cardiovascular and neurologic systems.

Measurement transducers are installed in a housing that is connectable to preselected conventional medical lines or catheters, such as urinary (foley), intravenous, arterial, cardiac or pulmonary catheters. The transducers detect a variety of bodily functions that may be transmitted to the catheters from within the body, such as patient heart beat, fetal heart beat, breathing, blood flow, labor contractions, ureteral flow and physiology of the bladder and other acoustic fields and dynamic pressure variations associated with the digestive, urologic, pulmonary, cardiovascular and neurologic systems.

The transducers, housing, electrical interface and signal processing electronics are positioned outside the body together with a variety of commercially available sterilized catheters that are inserted into the body. This facilitates use, improves patient safety, reduces the probability of infection, and eliminates the need for special procedures or personnel to install such off-the-shelf devices inside the body.

The transducer signals are stored by a data acquisition device for subsequent processing, analysis or display, or the signals may be processed, analyzed and displayed immediately to provide real time physiological monitoring.

More particularly, the novel method for measurement and analysis of bodily functions includes the steps of connecting a housing to the proximal end of a preselected medical catheter, inserting a distal end of the preselected medical catheter into a patient's body while maintaining the proximal end and the housing outside the patient's body, positioning at least one transducer within the housing so that said at least one transducer is in fluid communication with gaseous or liquid fluids in the patient's body, monitoring acoustic fields and pressure variations of liquid or gaseous fluids within the preselected medical catheter due to a variety of bodily functions, including patient heart beat, fetal heart beat, breathing, labor contractions, ureteral flow and physiology of the bladder, digestive, urologic, pulmonary, cardiovascular and neurologic systems, providing a data acquisition system for conditioning, amplifying and converting analog measurement signals generated by said at least one transducer to digital signals, positioning said data acquisition system externally of the housing, and providing electrical communication between said at least one transducer and said data acquisition system.

Further novel steps include mounting a Luer-type connector on a distal end of the housing, opening a valve mounted on the proximal end of the preselected catheter by employing the Luer-type connector to connect the housing to the proximal end of the preselected medical catheter, mounting a purge/fill valve on the housing so that gaseous or liquid fluids may be introduced into or purged from the housing, filling or purging the housing and preselected medical catheter with gaseous or liquid fluid when the valve mounted on the proximal end of the preselected catheter is opened by the Luer-type connector, and selecting said preselected medical catheter from a group of medical catheters including urinary (foley) catheters, intravenous catheters, arterial catheters, cardiac catheters, pulmonary catheters, bronchial catheters, esophageal catheters, and colon catheters.

In addition to post-attachment filling, the invention also includes the steps of filling the catheter without the device attached, followed by attaching the device so that the Luer-type connector provides fluid communication with the transducers.

Moreover, the invention also includes the "open-channel" case in which a Luer-type connector rather than a Luer-actuated valve is mounted on the proximal end of the catheter. The device is then attached with a Luer-activated valve on its proximal end and used for filling.

The novel method further includes the steps of providing said at least one transducer in the form of at least one acoustic transducer or at least one pressure transducer, or both selecting as said preselected medical catheter a urinary catheter having a balloon formed integrally therewith, connecting the housing to a proximal end of the urinary catheter, positioning a distal end of the urinary catheter within the bladder of a patient, and directly measuring acoustic fields and dynamic pressure variations in the gaseous or liquid fluid that fills the balloon with said at least one acoustic transducer and a least one pressure transducer.

The novel method also includes the steps of providing said at least one transducer in the form of at least one acoustic transducer or at least one pressure transducer, or both, selecting as said preselected medical catheter an intravenous catheter or arterial line, and monitoring and measuring fetal heart rates, fetal heart tones and a mother's heart rate with said at least one acoustic and pressure measurement transducers.

Further method steps include providing said at least one transducer in the form of at least one acoustic transducer or at least one pressure transducer, or both, selecting a urinary catheter as the preselected medical catheter, placing the drainage tube of the urinary catheter within the bladder of a patient, directly measuring acoustic fields and dynamic pressure variations in the bladder by connecting the housing to a proximal end of the drainage tube, and detecting ureteral flow and damage to the bladder wall which may occur during surgery with said at least one acoustic transducer and said at least one pressure transducer.

Additional method steps include providing said at least one transducer in the form of at least one acoustic transducer or at least one pressure transducer, or both, measuring acoustic fields and dynamic pressure variations in the cardiovascular system due to beating of the heart, vascular disease or other anomalies that can be detected through changes in blood flow by connecting the housing to the venous or arterial entry port of a peripherally inserted catheter, central catheter, or subcutaneous implantable port or manifold used in medical procedures.

Still further novels steps include providing said at least one transducer in the form of at least one acoustic transducer or at least one pressure transducer, or both, selecting a bronchial catheter as said preselected medical catheter, inserting a distal end of said bronchial catheter into a bronchial tube of a patient or any branches of said bronchial tube, and measuring acoustic fields and dynamic pressure variations in the lungs during breathing by connecting said housing to a proximal end of said bronchial catheter.

Another novel method includes the steps of providing said at least one transducer in the form of at least one acoustic transducer or at least one pressure transducer, or both, selecting a esophageal catheter as said preselected medical catheter, inserting a distal end of said esophageal/gastric catheter into the esophagus tube of a patient, and measuring acoustic fields, dynamic pressure variations and contractions in the stomach or upper digestive tract due to digestion by connecting the housing to the proximal end of said esophageal/gastric catheter.

Yet another novel method includes the steps of providing said at least one transducer in the form of at least one acoustic transducer or at least one pressure transducer, or both, selecting a colon catheter as said preselected medical catheter, inserting a distal end of said colon catheter into the colon of a patient, and measuring acoustic fields, dynamic pressure variations and contractions in the colon due to digestion by connecting said housing to the proximal end of said colon catheter.

All of the novel method steps include the step of providing said electrical communication through a wired or wireless transmission of transducer signals to said data acquisition system.

The novel method may also include the step of mounting a membrane within the housing to shield said at least one transducer from bodily fluids while allowing passage of acoustic and pressure variations and disturbances in the blood flow.

A data analysis system may also be provided and connected to said data acquisition system for processing digital measurement signals and for removing and isolating extraneous noises. The digital measurement signals are processed by said data acquisition system to monitor and analyze a variety of bodily functions, including patient heart beat, fetal heart beat, breathing, labor contractions, ureteral flow and physiology of the bladder, digestive, urologic, pulmonary, cardiovascular and neurologic systems. Raw or processed measurement signal data may be stored in a digital memory device and said stored raw or processed measurement signal data may be displayed in a graphical display.

The data acquisition system may be provided in the form of a hand-held computational device. Moreover, the housing may be covered with sound absorbing materials to shield it from ambient noise. Ambient noise may be actively cancelled by employing at least one external microphone in combination with said at least one transducer. Extraneous body noises or pressure fluctuations may be actively cancelled by positioning at least one acoustic or at least one pressure measurement transducer externally on a patient's body in combination with said at least one transducer.

The housing and said at least one transducer may be sterilized for subsequent use.

The housing and said at least one transducer may also be provided in disposable form and said at least one transducer may be provided in the form of a Doppler ultrasound transceiver. The housing may also be unsterilized but connected with a disposable sterilized connector and covered with a sterile, protective sheath.

An important object of this invention is to monitor a plurality of bodily functions during labor or surgical procedures without requiring the introduction of monitoring devices into the body of a patient.

BRIEF DESCRIPTION OF THE DRAWINGS

For a more complete understanding of the invention, reference should be made to the following detailed description, taken in connection with the accompanying drawings, in which.

DETAILED DESCRIPTION OF THE PREFERRED EMBODIMENT

Figure 1:
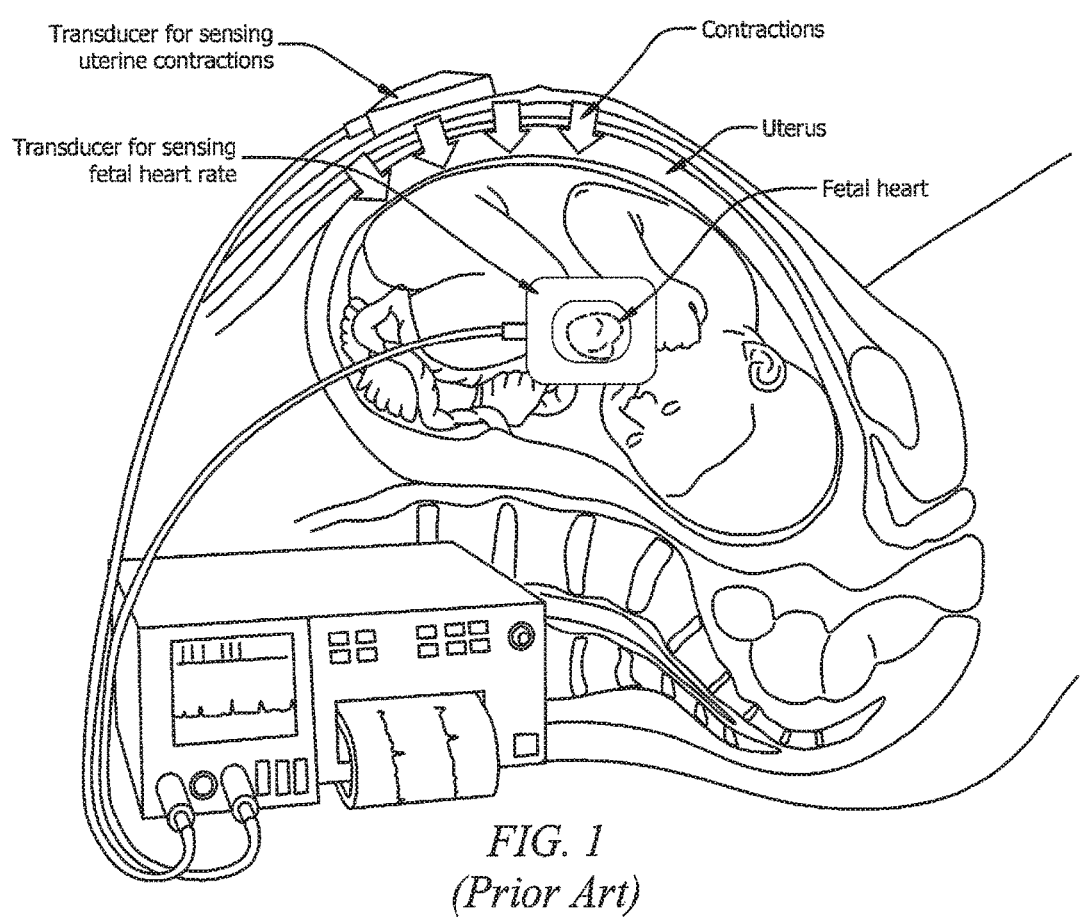
FIG. 1 is a diagram of a prior art external fetal monitor and its placement in monitoring a fetus.
Figure 2:
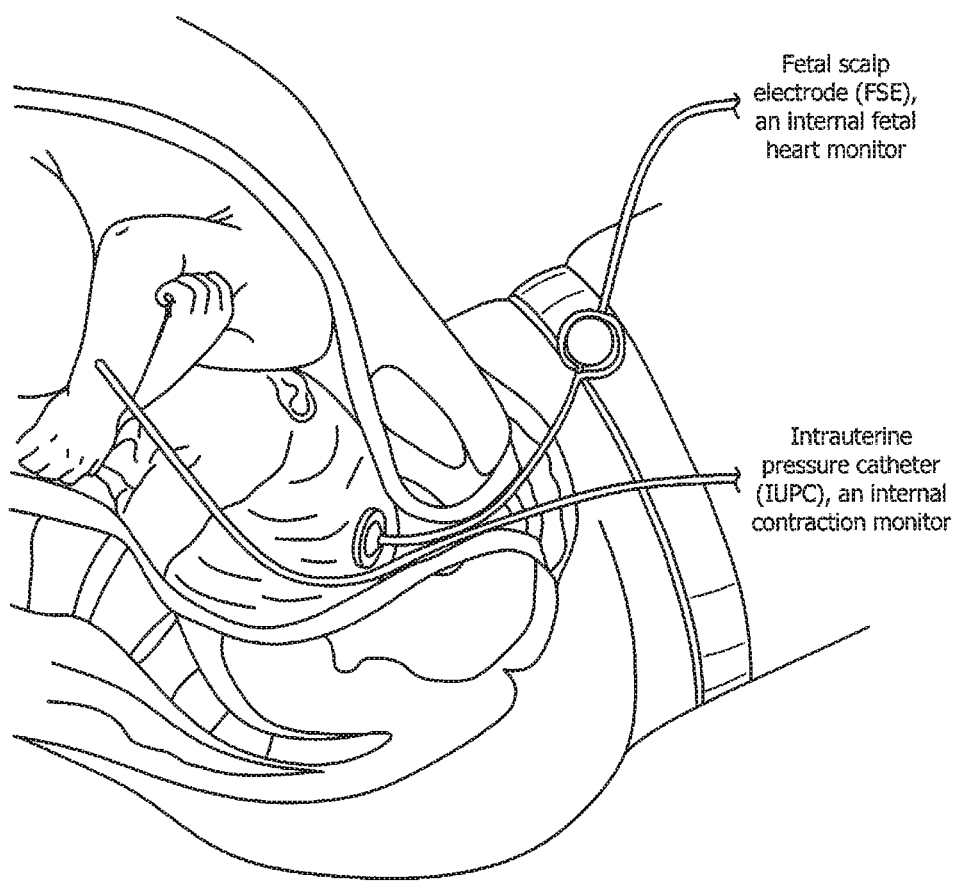
FIG. 2 is a diagram of a prior art internal fetal monitor and its placement in monitoring a fetus.
Figure 3:
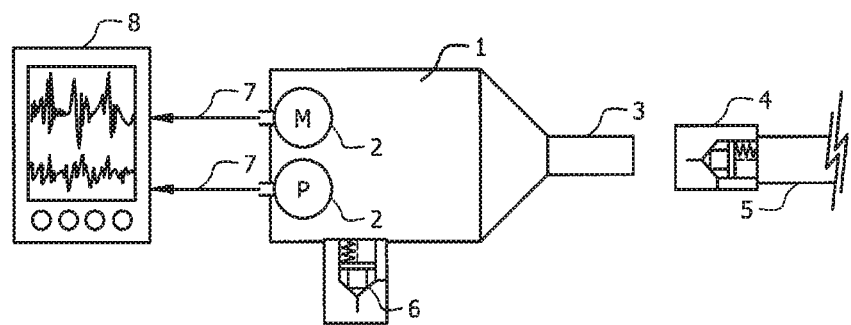
FIG. 3 is a diagram of an electronic catheter stethoscope.

The novel electronic catheter stethoscope is illustrated in FIG. 3. Housing 1, made from medical-grade plastic or metal or similar material, contains transducers 2. These transducers may include at least one acoustic measurement device such as a microphone or at least one pressure measurement device, or both, that operate in gaseous or liquid fluid.

Housing 1, transducers 2, electrical interface 7 and signal processing electronics 8 of this invention are used outside the body together with a variety of commercially-available off-the-shelf sterilized catheters that are inserted into the body. This facilitates use, improves patient safety, reduces the probability of infection, and eliminates the need for special procedures or personnel to install such devices inside the body.

The transducer signals may be stored by data acquisition device 8 for subsequent processing, analysis or display, or they may be processed, analyzed and displayed immediately to provide real-time physiological monitoring.

Housing 1 incorporates a standard medical Luer-type connector 3 that enables its connection to a variety of preselected tubes, valves and manifolds used in a variety of standard medical catheters or lines 5, such as urinary (foley), intravenous, arterial, bronchial/pulmonary, esophageal and colon catheters.

Luer-type connector 3 contains the gaseous fluid within the catheter system and also enables the opening of valve 4 that is installed in conventional medical catheter 5. Connector 3 enables a direct connection between transducers 2 and the liquids/gases or bodily fluids, or both, within catheter tube 5. Fill/Purge valve 6 enables filling and purging of gaseous or liquid fluids into and from housing 1, respectively.

Transducers 2 have sufficient dynamic range, frequency response and sensitivity to measure acoustic fields and dynamic pressure variations in the gaseous or liquid fluids inside catheter tube 5 that are present due to a variety of bodily functions, including patient heart beat, fetal heart beat, breathing, labor contractions, ureteral flow and physiology of the bladder, and other acoustic fields and dynamic pressure variations associated with the digestive, urologic, pulmonary, cardiovascular and neurologic systems.

Transducers 2 are connected through electronic interface 7 to data acquisition system 8 that acquires, analyzes, stores and displays the transducer data.

Figure 4:
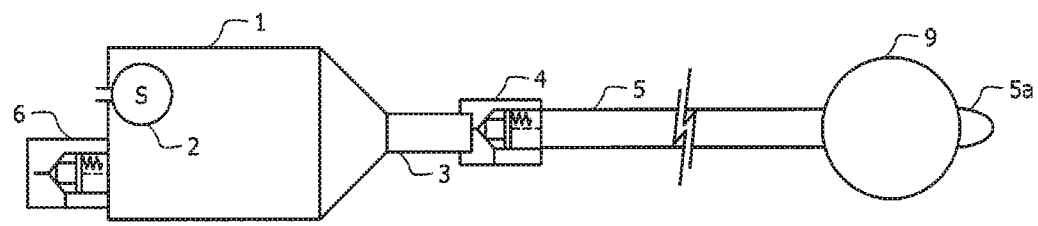
FIG. 4 is a diagram of the electronic catheter stethoscope used for a urinary (foley) catheter application.
Figure 5:
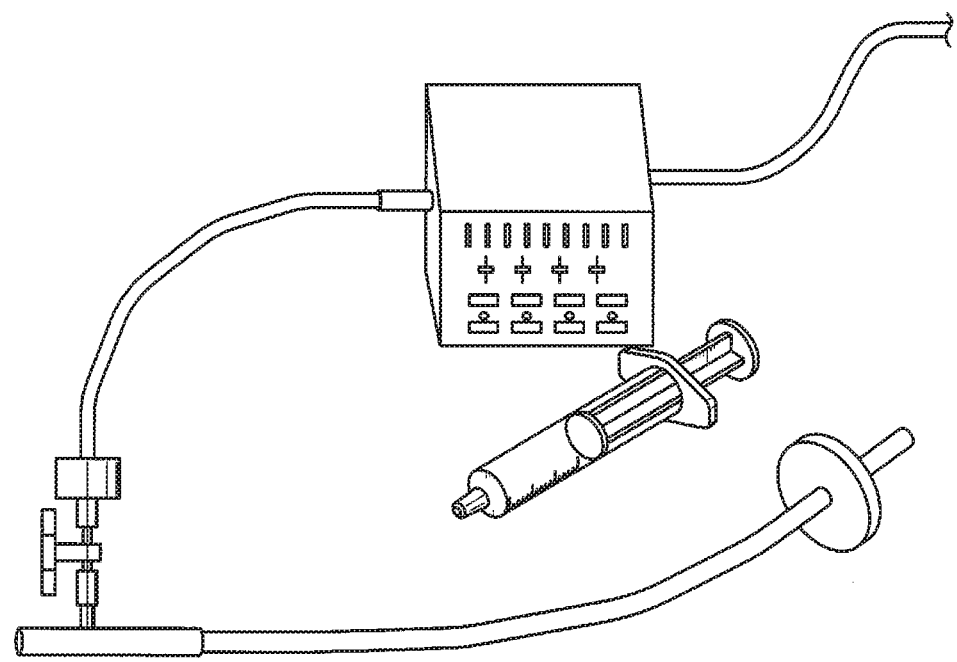
FIG. 5 is a perspective view of an electronic catheter stethoscope used for urinary (foley) catheter applications.

The novel method for monitoring labor and delivery includes the step of installing the novel electronic catheter stethoscope onto the external (proximal) end of a conventional urinary (foley) catheter, the distal end of which is placed within the mother's bladder, rectum or uterus during labor (FIGS. 4 & 5) for purposes of monitoring the fetal heart tones and mother's labor contractions. Due to the close anatomic relationship of the bladder, rectum or uterus to the fetus, information obtained from within these organs provide a more accurate way to measure uterine contractions and fetal heart tones.

The novel device is installed on the catheter balloon fill line so that catheter balloon 9 is in intimate contact with the mother's bladder. Catheter balloon 9 responds to sound and vibration from within the bladder due to the fetal heart beat, mother's heart beat and intrauterine contractions. Balloon 9 transmits this sound and vibration to the liquid or gaseous fluid that fills it, and through catheter tube 5 having tip 5a to the transducer or transducers 2. The transducer measurement device or devices 2 sense acoustic fields and dynamic pressure variations within the gaseous or liquid fluid, and convert said variations into corresponding varying electrical signals that are analyzed in data acquisition device 8.

Advantages of the invention compared to the prior art for labor and delivery monitors include the following:

- The monitoring system is external to the body. There is therefore less risk of infection or injury to the patient or baby as compared to internal monitors, and replacement of the device can easily be accomplished if malfunction occurs.
- Use of the device does not alter normal medical protocols or interfere with standard procedures.
- The device allows the monitoring of intrauterine contractions and fetal heart tones with a single instrument instead of two separate monitoring systems.
- The device is less susceptible than external monitors to mother's and baby's movement, excessive amniotic fluid and the mother's obesity. This enables continued monitoring of the fetal heart rate and intrauterine contractions on a wide range of medical conditions and does not require immobilization of the mother during usage.
- The device detects strength of contractions as well as contraction frequency and duration.
- The device does not commit the mother into labor and therefore can be used to monitor the baby internally at any time.

The novel method for monitoring bladder physiology includes the step of monitoring and detecting ureteral flow, urinary injury and abnormalities of bladder physiology during pelvic and urological surgery by means of the electronic catheter stethoscope. The electronic catheter stethoscope is connected to the valve that is used to fill the catheter balloon or on the catheter drainage line.

The electronic catheter stethoscope may also be connected to a catheter balloon fill valve. The catheter balloon is then positioned for intimate contact with the patient's bladder. Transducer measurement device or devices 2 sense acoustic fields and dynamic pressure variations within the gaseous or liquid fluid that is used to fill the catheter balloon, as the balloon responds to and transmits sound and vibration from within the bladder due to urine flow from the ureters and potential damage to the bladder wall which may occur during surgery.

If the electronic catheter stethoscope is connected to the catheter drainage line, transducers 2 directly sense potential damage to the ureters or bladder which may occur during surgery. In this case, the transducers sense a large increase in the acoustic levels from within the bladder due to damage of the bladder or ureter walls.

The novel method for cardiovascular monitoring includes connection of the electronic catheter stethoscope to an intravenous catheter or arterial line to monitor dynamic blood pressure and to measure and analyze heart tones, vascular changes, or both for the detection of heart valve anomalies, heart murmurs, valvular leaks, or vascular changes suggestive of cardiovascular disease or tumors.

The electronic catheter stethoscope is connected to the venous or arterial entry port of a peripherally inserted catheter, central catheter, or subcutaneous implantable port or manifold used in medical procedures in order to measure acoustic fields and dynamic pressure variations in the cardiovascular system due to beating of the heart, vascular disease or other anomalies that can be detected through changes in blood flow.

The novel method for bronchial monitoring includes the step of connecting the electronic catheter stethoscope to a bronchial or pulmonary catheter to monitor and analyze acoustic fields and dynamic pressure variations associated with respiration and blood flow within the pulmonary system.

The novel method for esophageal/gastric monitoring includes the step of connecting the electronic catheter stethoscope to an esophageal or gastric catheter or tube to monitor and analyze acoustic fields and dynamic pressure variations in the stomach or upper digestive tract due to digestion.

The novel method for colon monitoring includes the step of connecting the electronic catheter stethoscope to a colon catheter to monitor and analyze acoustic fields and dynamic pressure variations in the colon due to digestion.

It will be seen that the advantages set forth above, and those made apparent from the foregoing description, are efficiently attained and since certain changes may be made in the above construction and method steps without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A method for measurement and analysis of bodily functions using an electronic catheter stethoscope configured to connect to a plurality of types of catheters, comprising the steps of:

connecting a housing of said electronic catheter stethoscope to a valve of a medical catheter selected from said plurality of types of catheters, wherein the valve is disposed on a proximal end of said medical catheter, wherein a purge/fill valve is mounted on said housing;

inserting a distal end of said medical catheter into a patient's body while maintaining said proximal end and said housing outside the patient's body, wherein an interior of said medical catheter is in fluid communication with bodily fluids in said patient's body;

said housing enclosing at least one transducer therewithin so that said at least one transducer is in communication with said interior of said medical catheter of said medical catheter and thus also in fluid communication with said bodily fluids in said patient's body, said at least one transducer sensing an acoustic field, a pressure, or a combination thereof of gaseous or liquid fluids within said medical catheter;

introducing said gaseous or liquid fluids from said medical catheter into said housing through said purge/fill valve;

purging said gaseous or liquid fluids from said medical catheter from said housing through said purge/fill valve;

monitoring acoustic fields and pressure variations of said gaseous or liquid fluids within said medical catheter due to said bodily functions affecting said bodily fluids within said patient, wherein said gaseous or liquid fluids within said medical catheter are affected by changes in said bodily fluids within said patient's body and wherein said gaseous or liquid fluids within said medical catheter may include said bodily fluids as well depending on the bodily function being measured and analyzed;

providing a data acquisition system for conditioning, amplifying and converting analog measurement signals generated by said at least one transducer to digital signals;

positioning said data acquisition system externally of said housing; and providing electrical communication between said at least one transducer and said data acquisition system and said at least one transducer.

2. The method of claim 1, wherein said gaseous or liquid fluids within said catheter includes said bodily fluids.

3. The method of claim 1, further comprising the step of:
mounting a Luer-type connector on a distal end of said housing;
opening said valve mounted on said proximal end of said catheter by employing said Luer-type connector to connect said housing to said proximal end of said medical catheter.

4. The method of claim 3, further comprising the steps of:
filling or purging said housing and medical catheter with said gaseous or liquid fluids when said valve mounted on said proximal end of said catheter is opened by said Luer-type connector.

5. The method of claim 1, further comprising the steps of:
selecting said medical catheter from the group consisting of a urinary (foley) catheter, an intravenous catheter, an arterial catheter, a cardiac catheter, a pulmonary catheter, a bronchial catheter, an esophageal catheter, and a colon catheter.

6. The method of claim 5, further comprising the steps of:
providing said at least one transducer in the form of an acoustic transducer or a pressure transducer;
selecting as said medical catheter said urinary catheter having a balloon formed integrally therewith;
connecting said housing to a proximal end of said urinary catheter;
positioning a distal end of said urinary catheter within the bladder of a patient; and
directly measuring acoustic fields and dynamic pressure variations in said gaseous or liquid fluids that fill said balloon with said acoustic transducer and said pressure transducer.

7. The method of claim 1, further comprising the steps of:
selecting as said medical catheter an intravenous catheter or an arterial line;
inserting a distal end of said intravenous catheter or said arterial line into a blood vessel; and
monitoring and measuring fetal heartrates, fetal heart tones and a mother's heart rate with said at least one transducer by connecting said housing to a proximal end of said heart-monitoring catheter.

8. The method of claim 1, further comprising the steps of:
providing said electrical communication through a wired or wireless transmission of transducer signals to said data acquisition system.

9. The method of claim 1, further comprising the step of:
mounting a membrane within said housing to shield said at least one transducer from said gaseous or liquid fluids within said medical catheter while allowing passage of acoustic and pressure variations and disturbances in the blood flow.

10. The method of claim 1, further comprising the steps of:
providing a data analysis system;
connecting said data analysis system to said data acquisition system for processing digital measurement signals and for removing and isolating extraneous noises; and
processing said digital measurement signals with said data acquisition system to monitor and analyze said bodily functions.

11. The method of claim 10, further comprising the step of:
storing raw or processed measurement signal data in a digital memory device.

12. The method of claim 11, further comprising the step of:
displaying said stored raw or processed measurement signal data in a graphical display.

13. The method of claim 1, further comprising the step of:
providing said data acquisition system in the form of a hand-held computational device.

14. The method of claim 1, further comprising the step of:
covering said housing with sound absorbing materials to shield said housing from ambient noise.

15. The method of claim 1, further comprising the step of:
actively cancelling ambient noise by employing at least one external microphone in combination with said at least one transducer.

16. The method of claim 15, further comprising the step of:
actively cancelling extraneous body noises or pressure fluctuations by employing at least one acoustic or at least one pressure measurement transducer positioned externally on a patient's body in combination with said at least one transducer.

17. The method of claim 1, further comprising the step of:
providing said at least one transducer in the form of a Doppler ultrasound transceiver.

18. The method of claim 1, further comprising the step of:
providing said at least one transducer in the form of a single transducer capable of measuring both said acoustic fields and said pressure variations of said gaseous or liquid fluids within said catheter.

19. The method of claim 1, further comprising the step of:
providing said at least one transducer in the form of an acoustic transducer and a pressure transducer both enclosed within said housing and measuring said acoustic fields and said pressure variations, respectively.

20. The method of claim 1, further comprising the steps of:
disconnecting said housing of said electronic catheter stethoscope from said proximal end of said medical catheter; and
connecting said housing of said electronic catheter stethoscope to a proximal end of a second medical catheter selected from said plurality of types of catheters,
wherein said medical catheter and said second medical catheter have differing uses within said patient's body.

* * * * *